Figure 4:
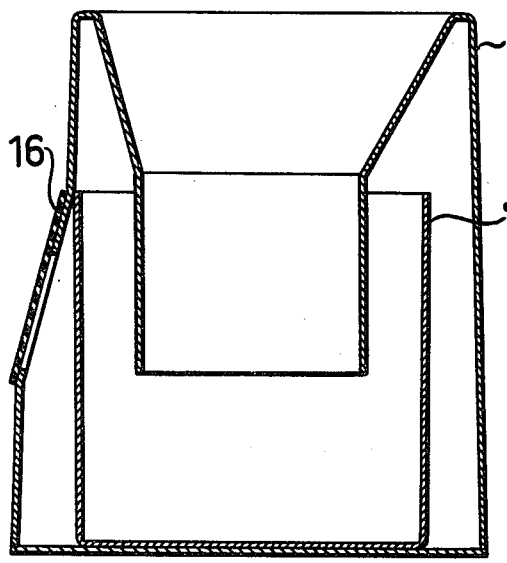

United States Patent [19]

Ritzler

[11] 4,097,381

[45] Jun. 27, 1978

[54] SEPARATOR WITH THROW-AWAY CONTAINER

[75] Inventor: Bo Ritzler, Sodertalje, Sweden

[73] Assignee: AB Filtrator, Sodertalje, Sweden

[21] Appl. No.: 772,105

[22] Filed: Feb. 25, 1977

[30] Foreign Application Priority Data

Feb. 27, 1976 Sweden .............................. 7602722

[51] Int. Cl.² .......................................... B01D 21/26
[52] U.S. Cl. .................................. 210/259; 55/429;
55/459 R; 210/512 R; 210/513
[58] Field of Search .................. 210/512 R, 513, 259,
210/84; 55/395, 421, 429, 459 R; 209/144, 211

[56] References Cited

U.S. PATENT DOCUMENTS

| 2,252,581 | 8/1941 | Saint-Jacques ............... 55/459 R X |
| 2,397,980 | 4/1946 | Petri ................................ 55/429 X |
| 3,151,961 | 10/1964 | Blackmore et al. ......... 210/512 R X |
| 3,621,641 | 11/1971 | Takei et al. ....................... 55/472 X |
| 3,988,133 | 10/1976 | Schady .............................. 55/459 R |

Primary Examiner—William A. Cuchlinski, Jr.
Attorney, Agent, or Firm—Wegner, Stellman, McCord, Wiles & Wood

[57] ABSTRACT

An apparatus for separating solid particles from a liquid carrying the solid particles. The liquid carrying the solid particles enters a cylindrical chamber having an upper portion with an air evacuation opening. The liquid flows down the sides of the chamber onto a funnel-shaped member. An exchangeable collecting vessel is positioned below the funnel-shaped member and retains and collects solid particles which precipitate out from the liquid. The liquid flows through an opening to a drainage container. The exchangeable collecting vessel has a self-closing resilient membrane covering its opening. The resilient membrane is pierced by a wedge-shaped projection at the drain opening when the collecting vessel is in position. When the collecting vessel is removed, the opening is closed by the resilient membrane to form a hygienic seal.

4 Claims, 6 Drawing Figures

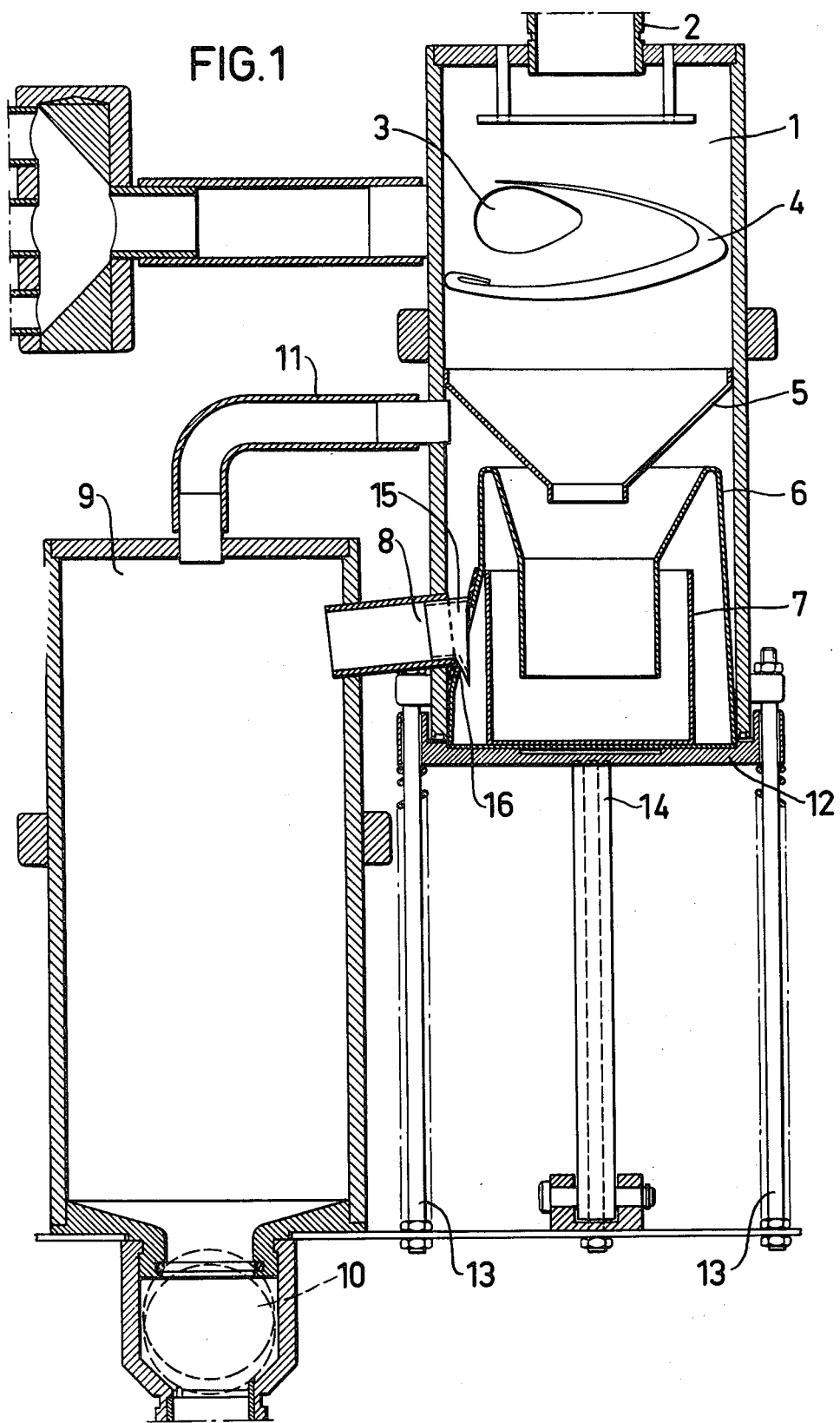

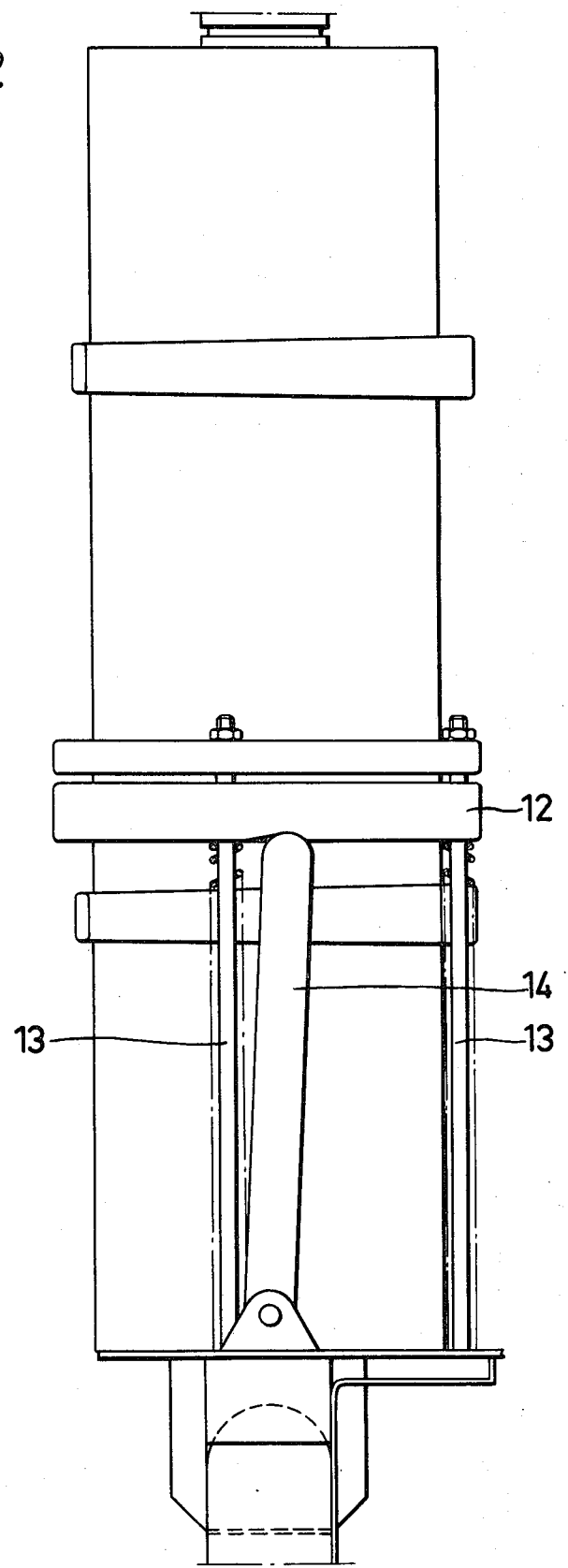

SEPARATOR WITH THROW-AWAY CONTAINER

This invention relates to a device for separating solid particles from a fluid containing one or more components in liquid and/or gaseous state. Such a separation is desire, for example, when solid particles of valuable material in a liquid are to be recovered or the emission of particles consisting of substances detrimental to the enivronment is to be prevented. It is often desirable at a separation facility to handle the collected substances in a hygienic satisfactory manner.

Swedish patent specification No. 7210957-2 discloses a separating device comprising a substantially cylindric separation chamber, which in its upper portion is provided with a feed opening and an air evacuation opening, and a lower portion having a drainage opening. Solid particles are collected in two places: heavy particles in an annular groove, and light particles downwardly in a collecting cup. The emptying and cleaning operations, however, are relatively tedious and less satisfactory from a hygienic aspect.

These problems are solved by the present invention that in the separation chamber between the feed and the drainage opening is attached a funnel-shaped member, which opens above the feed opening to an exchangeable collecting vessel attached in the lower portion of the chamber and with its outlet opening sealingly connected to said drainage opening of the chamber. The oulet opening of the collecting vessel preferably is provided with a self-closing rubber membrane.

Figure 5:
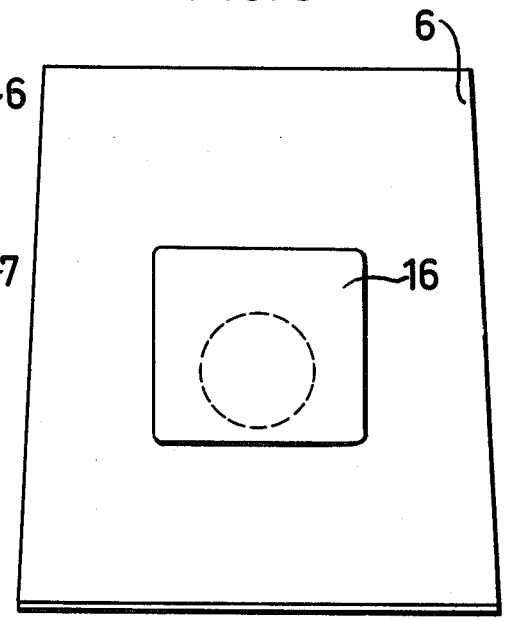
Figure 6:
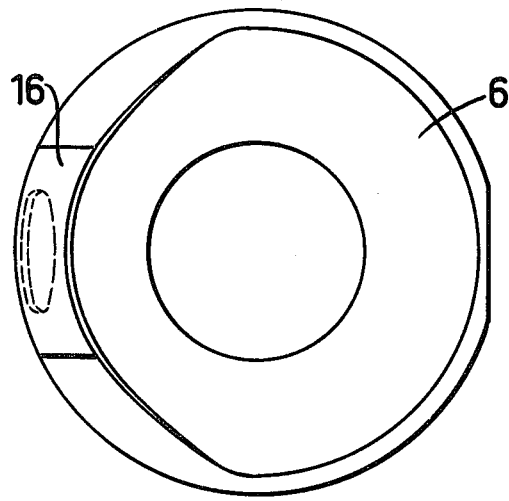
Figure 3:
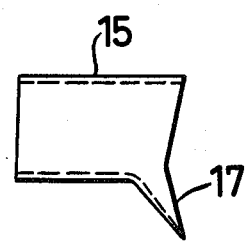

An embodiment of the invention is described in greater detail in the following, with reference to the drawings, in which FIG. 1 is a cross-sectional front view of a device according to the invention, FIG. 2 is a side view of the device in FIG. 1, FIG. 3 shows an embodiment of a bushing utilized in the device according to FIG. 1, FIG. 4 is a cross-sectional front view of an embodiment of a collecting vessel utilized in the device of FIG. 1, FIG. 5 is a lateral view of the vessel in FIG. 4, and FIG. 6 is a top view of the vessel in FIG. 4.

According to the invention, the device shown in FIGS. 1 and 2 is intended to be used for dental purposes in the separation of air, cooling liquid, saliva and solid particles, as amalgam removed by drilling during the treatment. The device comprises a separation chamber 1, which via a pipe 2 is connected to a vacuum source (not shown). The separation chamber 1 is provided with a feed opening 3, the connecting pipe of which feeds saliva etc. substantially tangentially along the inner wall of the cylindrical separation chamber. A guide bar 4 guides the supplied mixture in a helical path downward in the separation chamber, and in connection with said movement air escapes from the mixture.

Within the separation chamber a funnel 5 is provided to direct the mixture into the inlet opening of a collecting vessel 6, which inwardly is provided with catching walls to ensure the separation of solid particles from the liquid by sedimentation. Due to the supplied mixture being guided in a helical path, it is braked and has an insignificant kinetic energy when it leaves the funnel 5. Hereby a calm and continuous supply to the collecting vessel 6 is ensured, which creates optimum conditions for the sedimentation process in said vessel. The collecting vessel, as is described below in greater detail, includes an outlet opening, which is sealingly connected to the drainage opening 8 of the separation chamber, which latter opening in its turn is connected to a drainage container 9. Container 9 is connected in its lower portion to the drainage mains via a check valve 10, and its upper portion is connected to the separation chamber 1 via a pressure balancing duct 11.

The bottom plate 12 of the separation chamber 1 can be moved upwardly and downwardly on guide means 13 and sealingly be locked in its upper position by means of a pivotal cotter pin 14, thereby rendering it possibly to easily exchange the collecting vessel 6, which is of throw-away type. The outlet opening of the collecting vessel 6 is, during operation, tightly connected to the drainage opening 8 of the separation chamber, and for hygienic reasons the outlet opening of the vessel 6 is self-closing when the vessel is removed from the separation chamber. This is achieved in that the drainage opening of the separation chamber 1 is provided with a bushing 15 and intended to cooperate with the collecting vessel 6 shown in FIG. 4, the outlet opening of which vessel is covered by a rubber membrane 16. When the vessel 6 is to be positioned in the separation chamber 1, it contains a certain amount of oil, for example a mineral oil, which in operation will lie above the liquid mixture in the vessel 6 and constitute a smell trap. The vessel 6 is positioned on the bottom plate 12, which is moved up to its upper position and there locked by the cotter pin 14. When the vessel 6 has arrived at a position at which the projecting pointed end 17 of the bushing 15 contacts the rubber membrane 16, the membrane is punctured and thereafter places itself as a sealing about the bushing 15, thereby providing a sealing between the outlet openings of the vessel 6 and chamber 1. When the vessel 6 is removed from the chamber 1, the rubber membrane 16 tends to re-assume its original shape and thereby closes the outlet mouth of the vessel 6.

The embodiment described above specifically relates to a device for dental use. Within the scope of the attached claims, however, a great number of different applications can be imagined, for example in the chemical-technical industry or drug industry, in such cases when prior to the discharge of drainage liquid sedimentable substances are to be separated and be handled in a hygienically satisfactory manner.

What I claim is:

1. A device for separating solid particles from a fluid carrying the particles comprising a substantially cylindrical separation chamber having an upper portion including a feed opening for receiving the fluid carrying the particles, an air evacuation opening for providing a vacuum to said separation chamber, and a lower portion having a drainage opening through which the fluid may be drained; a funnel-shaped member secured to the separation chamber disposed between the feed opening and the drainage opening; an exchangeable collecting vessel for collecting and retaining the particles, said collecting vessel having an inlet opening located below the funnel-shaped member and an outlet having a self-closing resilient membrane thereacross; and means for piercing said resilient membrane and for sealably engaging it with the drainage opening.

2. The device of claim 1 wherein said means for piercing said resilient membrane and for sealably engaging it with the drainage opening includes a bushing having a pointed wedge-shaped projection, which bushing and resilient membrane form a seal between the outlet and the drainage opening.

3. The device of claim 1 further including a drainage container having a lower portion which is connected through a check valve to a drainage main and an upper portion connected through a pressure balancing duct to the separation chamber below the funnel-shaped member.

4. The device of claim 1, wherein the feed opening of the chamber is connected to a feed pipe supplying the fluid with solid particles tangentially along an inner wall of the chamber where the fluid is guided downwardly by a helical guide bar attached on the chamber.

* * * * *